US00PP09512P

United States Patent [19]

Olij

[11] Patent Number: Plant 9,512

[45] Date of Patent: Apr. 23, 1996

[54] FLORIBUNDA ROSE PLANT NAMES 'OLYSKO'

[75] Inventor: Huibert W. Olij, De Kwakel, Netherlands

[73] Assignee: The Conard-Pyle Company, West Grove, Pa.

[21] Appl. No.: 399,927

[22] Filed: Mar. 7, 1996

[51] Int. Cl.[6] ..... A01H 5/00

[52] U.S. Cl. ..... Plt./24

[58] Field of Search ..... Plt./15, 24

[56] References Cited

U.S. PATENT DOCUMENTS

P.O. 3,975 11/1976 Jelly ..... Plt/24

P.O. 7,362 10/1990 de Ruiter ..... Plt/18

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly forms attractive double intense yellow blossoms which are long-lasting when cut and placed in a vase. The foliage is dark green and exhibits a glossy upper surface that contrasts well with the light blossom coloration. The plant exhibits vigorous vegetation and exhibits an erect growth habit. The new variety is well suited for cut flower production under greenhouse growing conditions.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Korflapei variety (U.S. Plant Pat. No. 6,695). The male parent (i.e., the pollen parent) of the new variety was the Ruidriko variety (U.S. Plant Pat. No. 7,362). The parentage of the new variety can be summarized as follows:

KorflapeixRuidriko.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive long-lasting double blossoms having an intense yellow coloration, (b) forms attractive vigorous dark green foliage having a glossy upper surface.

(c) exhibits an erect growth habit, and (d) is well suited for cut flower production in a greenhouse.

As demonstrated in France, the new variety undergoes asexual propagation of a number of routes, including budding, grafting, cuttage, etc. The characteristics of the new variety have been found to be strictly transmissible by such asexual propagation from one generation to another in France.

The new variety has been named the Olysko variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France.

DETAILED DESCRIPTION

Figures 1, 2, 3, 4, 5, 6, 7, 8, 9, 10, 11, 12, 13, 14, 15, 16:
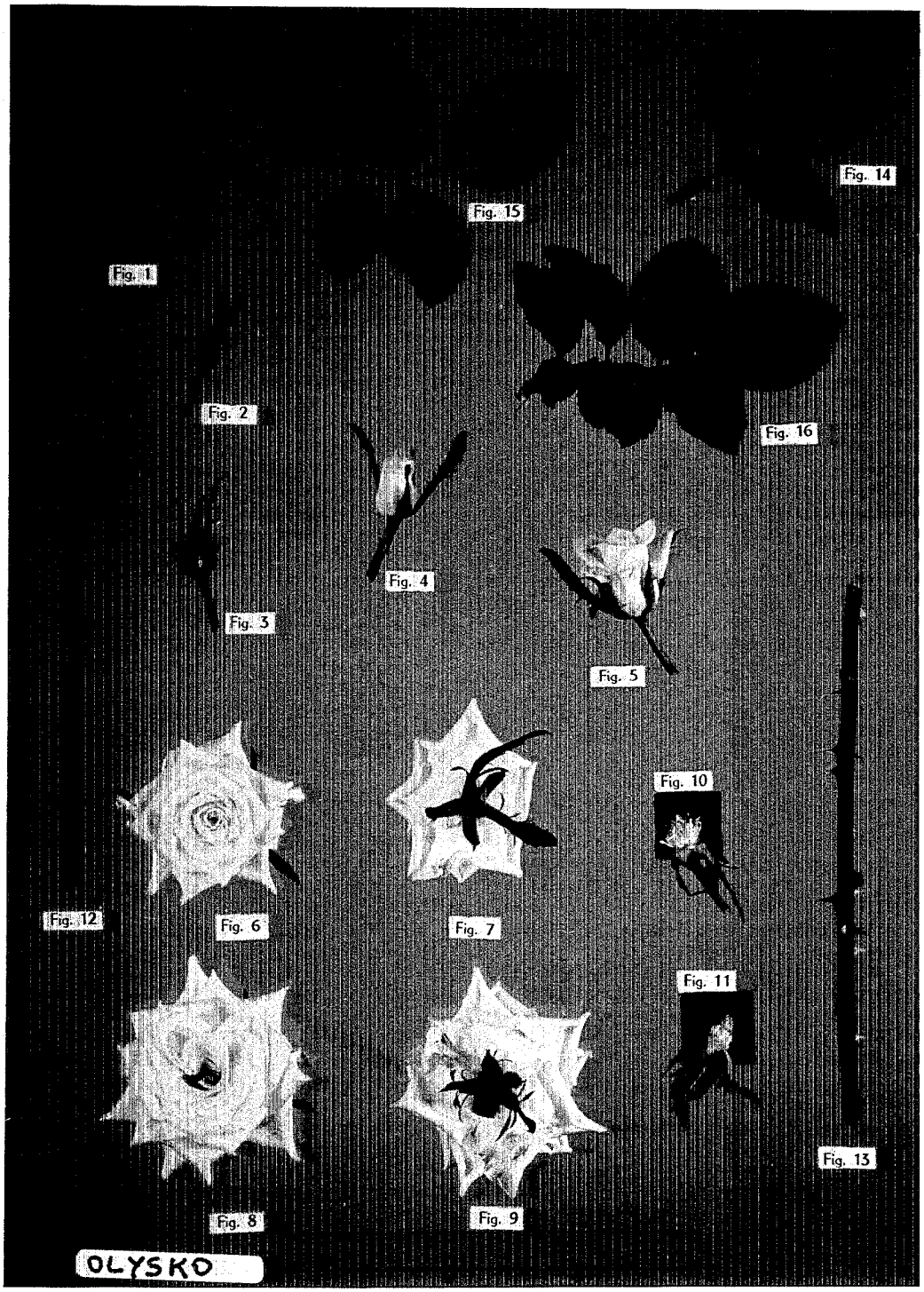
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates the specimen of a flower in the course of opening.
FIG. 6 illustrates a specimen of an open flower— plan view—obverse.
FIG. 7 illustrates a specimen of an open flower— plan view—reverse.
FIG. 8 illustrates a specimen of a fully open flower— plan view—obverse.
FIG. 9 illustrates a specimen of a fully open flower— plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of an adult main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of a Royal Horticultural Society (R.H.S. Colour Chart). The terminology which precedes reference to the chart has been added to indicate the corresponding color in more common terms. The description is based on three year-old specimens of the new variety during September while budded on *Rosa indica* understock and growing in greenhouses in Le Cannet des Maures, Var, France.

Class: Floribunda.

Plant:

*Height.*—Approximately 40 to 50 cm on average at the end of the growing season.

*Habit.*—erect.

Branches:

*Color.*—Young stems: medium green, Green Group 136B. Adult Wood: medium green, Green Group 139A.

*Thorns.*—Size: medium. Quantity: medium Color: greenish on young stems, and light brown on mature wood (as illustrated).

Leaves:

*Stipules.*—Adnate, pectinate, rather wide and linear.

*Petioles.*—Upper surface: striped reddish brown on young foliage and medium green on adult foliage. Under surface: light green, with some small thorns.

*Leaflets.*—Number: 3, 5 (most often), and 7. Shape: oval. Serration: single and regular. Texture: very consistent. General appearance: dense, dark and bright foliage. Color (young foliage): Upper surface: dark medium green, Green Group 136B, and more or less stained with reddish coloration. Under surface: medium green, Green Group 136C, and more or less stained with reddish coloration. Color (adult foliage): Upper surface: dark green, Green Group 139B. Under surface: medium green, Green Group 137B and widely suffused with reddish coloration.

Inflorescence:

*Number of flowers.*—Usually one to three blooms per stem.

*Peduncle.*—Medium green in coloration, and approximately 6 to 8 cm. in length on average.

*Sepals.*—Upper surface: tomentose and greenish in coloration. Under surface: light green in coloration and the outer sepals commonly have many small appendiculate edges.

*Buds.*—Shape: conical. Length: approximately 2.5 cm. on average. Size: large. Color upon opening: Upper surface: Bright Yellow, Yellow Group 7A. Under surface: Sulphur Yellow, Yellow Group 6C with more or less greenish coloration on the external petals.

*Flower.*—Shape: cup-shaped with substantially parallel edges, and double. Diameter: approximately 8 cm. on average. Color (when opening begins): Upper Surface: Canary Yellow, Yellow Group 9C, and Lemon Yellow, Yellow Group 12B towards the base. Under surface: Sulphur Yellow, Yellow Group 6C; lighter on the outer petals; and Lemon Yellow, Yellow Group 12B towards the base. Color (when blooming): Upper surface: Canary Yellow, Yellow Group 9C; Lemon Yellow, Yellow Group 12B towards the base; and Lemon Yellow, Yellow Group 13A on the inner petals. Under surface: Sulphur Yellow, Yellow Group 6C; lighter on the outer petals; Lemon Yellow, Yellow Group 12B towards the base; and Light Lemon Yellow, Yellow- Orange Group 14C on the inner petals. Color (at end of opening): Upper Surface: Canary Yellow: Yellow Group 9C; Lemon Yellow, Yellow Group 12B towards the base; and Lemon Yellow, Yellow Group 13A on the inner petals. Under surface: Sulphur Yellow, Yellow Group 6C; lighter on the outer petals; Lemon Yellow, Yellow Group 12B towards the base; and Light Lemon Yellow, Yellow-Orange Group 14C on the inner petals. Fragrance: none. Lasting quality: very long lasting blossoms when cut and placed in a vase. Petal drop: very good. Petal form: oval with reflexed edges. Stamen number: approximately 72 on average. Anthers: normal and golden yellow in coloration. Filaments: greenish and yellowish in coloration and commonly tend to be of irregular heights. Pistils: apaproximately 15 to 20 on average. Stigmas: normal, straw-like, and sometimes possess a vegetative center. Styles: tomentose near the base, and greenish in coloration. Receptacle: medium green, smooth, and in longitudinal section in the shape of a wide funnel.

Development:

*Vegetation.*—Vigorous.

*Blooming.*—Very abundant.

*Resistance to disease.*—Very good.

I claim:

1. A new and distinct variety of Floribunda rose plant characterized by the following combination of characteristics:

(a) forms in abundance attractive long-lasting double blossoms having an intense yellow coloration, (b) forms attractive vigorous dark green foliage having a glossy upper surface, (c) exhibits an erect growth habit, and (d) is well suited for cut flower production in a greenhouse; substantially as herein shown and described.

* * * * *

OLYSKO

UNITED STATES PATENT AND TRADEMARK OFFICE

CERTIFICATE OF CORRECTION

PATENT NO. : PLANT 9,512

DATED : April 23, 1996

INVENTOR(S) : Huibert W. Olij

It is certified that error appears in the above-indentified patent and that said Letters Patent is hereby corrected as shown below: On the title page:

Item [54] and column 1, should read --FLORIBUNDA ROSE PLANT NAMED 'OLYSKO'--

At [22] please change the date of filing from "March 7, 1996" to --March 7, 1995--.

Signed and Sealed this

Sixteenth Day of July, 1996

*Attest:*

*Attesting Officer*

BRUCE LEHMAN

*Commissioner of Patents and Trademarks*